(12) United States Patent
Netzel et al.

(10) Patent No.: US 11,123,093 B2
(45) Date of Patent: Sep. 21, 2021

(54) JAW DRIVE ARM FOR SURGICAL INSTRUMENTS AND SURGICAL INSTRUMENTS INCORPORATING THE SAME

(71) Applicant: COVIDIEN LP, Mansfield, MA (US)

(72) Inventors: Kenneth E. Netzel, Loveland, CO (US); Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 259 days.

(21) Appl. No.: 16/505,831

(22) Filed: Jul. 9, 2019

(65) Prior Publication Data

US 2021/0007763 A1   Jan. 14, 2021

(51) Int. Cl.
*A61B 17/295* (2006.01)
*A61B 17/32* (2006.01)
*A61B 17/29* (2006.01)

(52) U.S. Cl.
CPC .... *A61B 17/295* (2013.01); *A61B 2017/2926* (2013.01); *A61B 2017/2947* (2013.01); *A61B 2017/320074* (2017.08); *A61B 2017/320094* (2017.08)

(58) Field of Classification Search
CPC ....... A61B 2017/320094; A61B 2017/320092; A61B 2017/320074; A61B 2017/2947; A61B 2017/2936; A61B 2017/2939; A61B 17/295
See application file for complete search history.

(56) References Cited

U.S. PATENT DOCUMENTS

| | | | |
|---|---|---|---|
| 6,063,103 A * | 5/2000 | Hashiguchi | A61B 17/29 606/205 |
| 6,214,023 B1 | 4/2001 | Whipple et al. | |
| 7,799,045 B2 | 9/2010 | Masuda | |
| 7,846,155 B2 | 12/2010 | Houser et al. | |
| 2009/0090765 A1* | 4/2009 | Blier | A61B 17/07207 227/176.1 |
| 2010/0063526 A1 | 3/2010 | Beaupre et al. | |
| 2012/0116396 A1 | 5/2012 | Price et al. | |
| 2012/0116433 A1 | 5/2012 | Houser et al. | |

(Continued)

OTHER PUBLICATIONS

Extended European Search Report issued in corresponding European Application No. 20184751.4 dated Nov. 6, 2020, 7 pages.

*Primary Examiner* — Darwin P Erezo
*Assistant Examiner* — Brigid K Byrd
(74) *Attorney, Agent, or Firm* — Carter, DeLuca & Farrell LLP (57) ABSTRACT

A surgical instrument includes an elongated body operably connected to a jaw member and a blade. The elongated body includes an inner tube and an outer tube configured to move laterally with respect to one another. A drive arm has a first end engaged to the outer tube and a second end pivotably coupled to the jaw member configured to move laterally in tandem with the outer tube such that motion of the outer tube in a first direction pulls the jaw member away from the blade, and motion of the outer tube in a second direction pushes the jaw member towards the blade. The drive arm includes a semi-rigid material configured to flex when compressed, such that flexion of the drive arm can offload excess force exerted by the outer tube on the jaw member.

14 Claims, 6 Drawing Sheets

(56) References Cited

U.S. PATENT DOCUMENTS

| | | | |
|---|---|---|---|
| 2012/0277762 A1* | 11/2012 | Lathrop | A61B 34/70 606/130 |
| 2014/0135804 A1 | 5/2014 | Weisenburgh, II et al. | |
| 2016/0345994 A1 | 12/2016 | Allen, IV | |
| 2018/0042637 A1 | 2/2018 | Craig et al. | |
| 2019/0133629 A1* | 5/2019 | Williams | A61B 17/122 |

* cited by examiner

FIG. 5B

JAW DRIVE ARM FOR SURGICAL INSTRUMENTS AND SURGICAL INSTRUMENTS INCORPORATING THE SAME

FIELD

The present disclosure relates to surgical instruments and, more particularly, to jaw drive arms of energy-based surgical instruments and energy-based surgical instruments incorporating the same.

BACKGROUND

Many energy-based surgical instruments employ an end effector configured to effectuate opening and closing of a jaw member to thereby facilitate clamping, manipulating, and/or applying energy to tissue to treat tissue.

Ultrasonic surgical instruments, for example, utilize ultrasonic energy in the form of ultrasonic vibrations to coagulate, cauterize, fuse, seal, cut, desiccate, fulgurate, and/or otherwise treat tissue. The ultrasonic energy is typically produced by a generator and transducer and is transmitted along a waveguide to an end effector of the ultrasonic surgical instrument. The end effector may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a surgical instrument including a jaw member and a blade. The jaw member is pivotably supported by an inner tube that is enclosed within an outer tube configured to move longitudinally about the inner tube. A drive arm having a first end portion is engaged with the outer tube. The drive arm has a second end portion that defines a lumen configured to receive a pivot pin. The pivot pin is rotatably disposed within the lumen and includes ends extending outwardly from each end of the lumen. The ends of the pivot pin are engaged with the jaw member such that longitudinal translation of the outer tube about the inner tube in a first direction pulls the jaw drive arm and the pivot pin to thereby pivot the jaw member away from the blade. Longitudinal translation of the outer tube about the inner tube in a second direction pushes the jaw drive arm and the pivot pin to thereby pivot the jaw member towards the blade.

In aspects, the jaw drive arm includes a semi-rigid material configured to flex when compressed beyond a predefined threshold force.

In aspects, the flexion of the drive arm is configured to offload the pushing force exerted by the outer tube on the jaw member when a pushing force of the outer tube is greater than the predefined threshold force of the drive arm.

In aspects, at least one protruding element is disposed on the first end portion of the drive arm and configured to be inserted into at least one fastening aperture defined within the outer tube.

In aspects, the at least one fastening aperture is configured to releasably receive the at least one protruding element such that the jaw drive arm is removably engaged to the outer tube.

In aspects, the at least one protruding element is welded within the at least one fastening aperture such that the drive arm is permanently engaged to the outer tube.

In aspects, the jaw member includes a proximal flange portion and a distal body portion extending distally from the proximal flange portion. The proximal flange portion defines a pair of spaced-apart flanges.

In aspects, each proximal flange of the proximal flange portion defines a groove configured to receive one of the ends of the pivot pin.

In aspects, the ends of the pivot pin are welded into the grooves such that the pivot pin is permanently affixed to the proximal flange portion of the jaw member.

In aspects, the pivot pin is freely rotatable within the pivot lumen of the jaw drive arm.

In aspects, a spacing between the proximal flanges of the proximal flange portion is greater than a width of the second end portion of the drive arm, and less than a length of the pivot pin.

In aspects, the drive arm tapers in thickness along at least a portion of a length thereof from the first end portion toward the second end portion.

In aspects, the first end portion of the drive arm is wider than the second end portion of the drive arm.

In aspects, the drive arm tapers inward along at least a portion of the length thereof from the first end portion towards the second end portion.

BRIEF DESCRIPTION OF THE DRAWINGS

The above and other aspects and features of the present disclosure will become more apparent in view of the following detailed description when taken in conjunction with the accompanying drawings, wherein.

DETAILED DESCRIPTION

Figure 1:
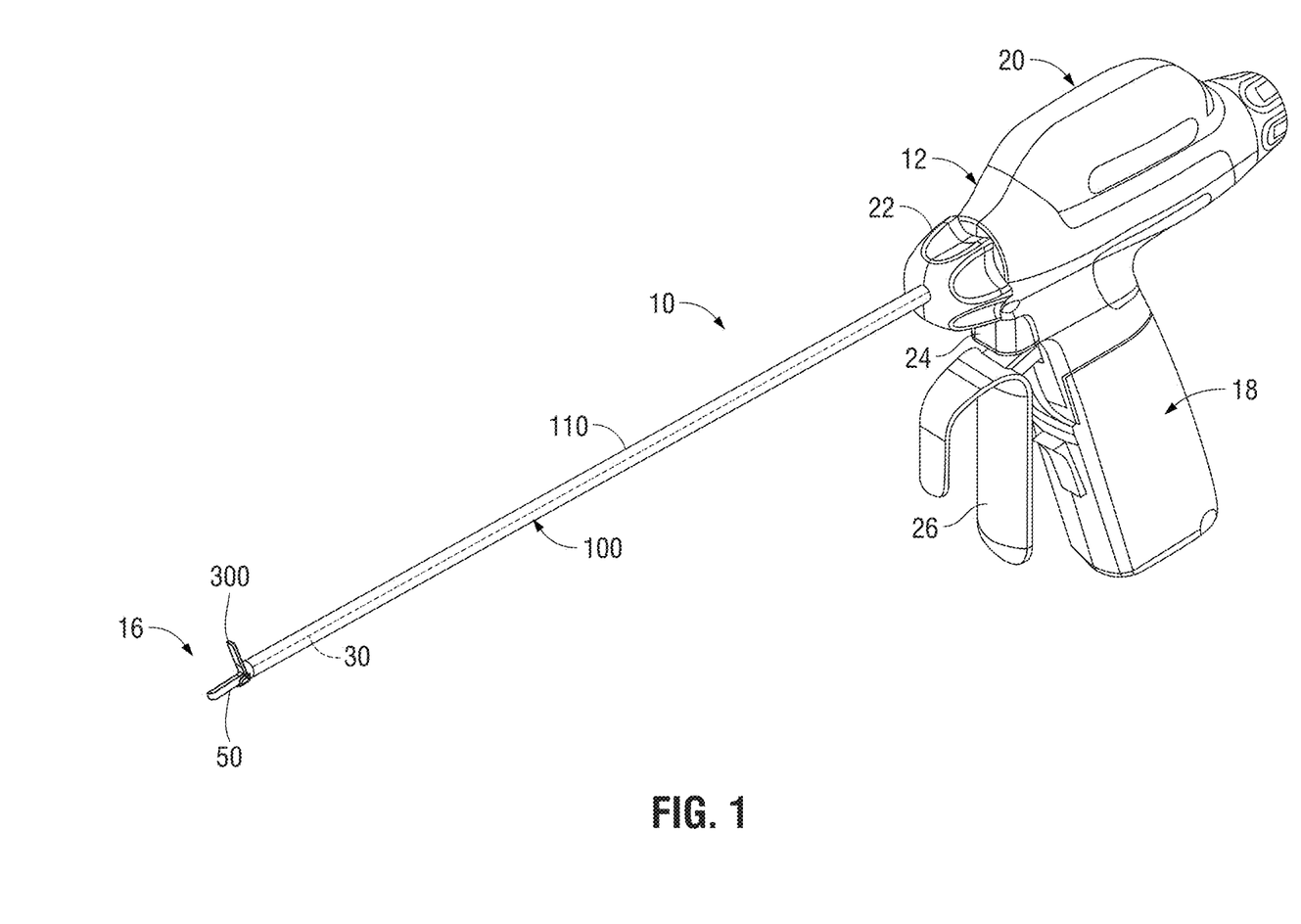
FIG. 1 is a perspective view of an ultrasonic surgical instrument including an end effector disposed in an open position.

Jaw drive arms and surgical instruments including such jaw drive arms are provided in accordance with the present disclosure and detailed hereinbelow. Referring to FIG. 1, although the jaw drive arms of the present disclosure are described for use with an ultrasonic surgical instrument 10, the jaw drive arms of the present disclosure may alternatively be configured for use with any other suitable jawbased surgical instrument, including ultrasonic surgical instruments different from ultrasonic surgical instrument 10.

Ultrasonic surgical instrument 10 generally includes a handle assembly 12, an elongated body portion 100, and an end effector 16. Handle assembly 12 supports a power supply, e.g., a battery assembly 18, and an ultrasonic transducer and generator assembly ("TAG") 20, although ultrasonic surgical instrument 10 may alternatively be configured as a tethered instrument wherein the power supply and generator are remote components coupled to handle assembly 12 via one or more surgical cables (not shown). Handle assembly 12 includes a rotation wheel 22, an activation button 24, and a clamp trigger 26. Battery assembly 18 and TAG 20 are each releasably coupled to handle assembly 12 and are removable therefrom to facilitate disposal of any disposable components, e.g., handle assembly 12, elongated body portion 100, and/or end effector 16, and reprocessing of any reusable components, e.g., battery assembly 18 and TAG 20.

Figure 2:
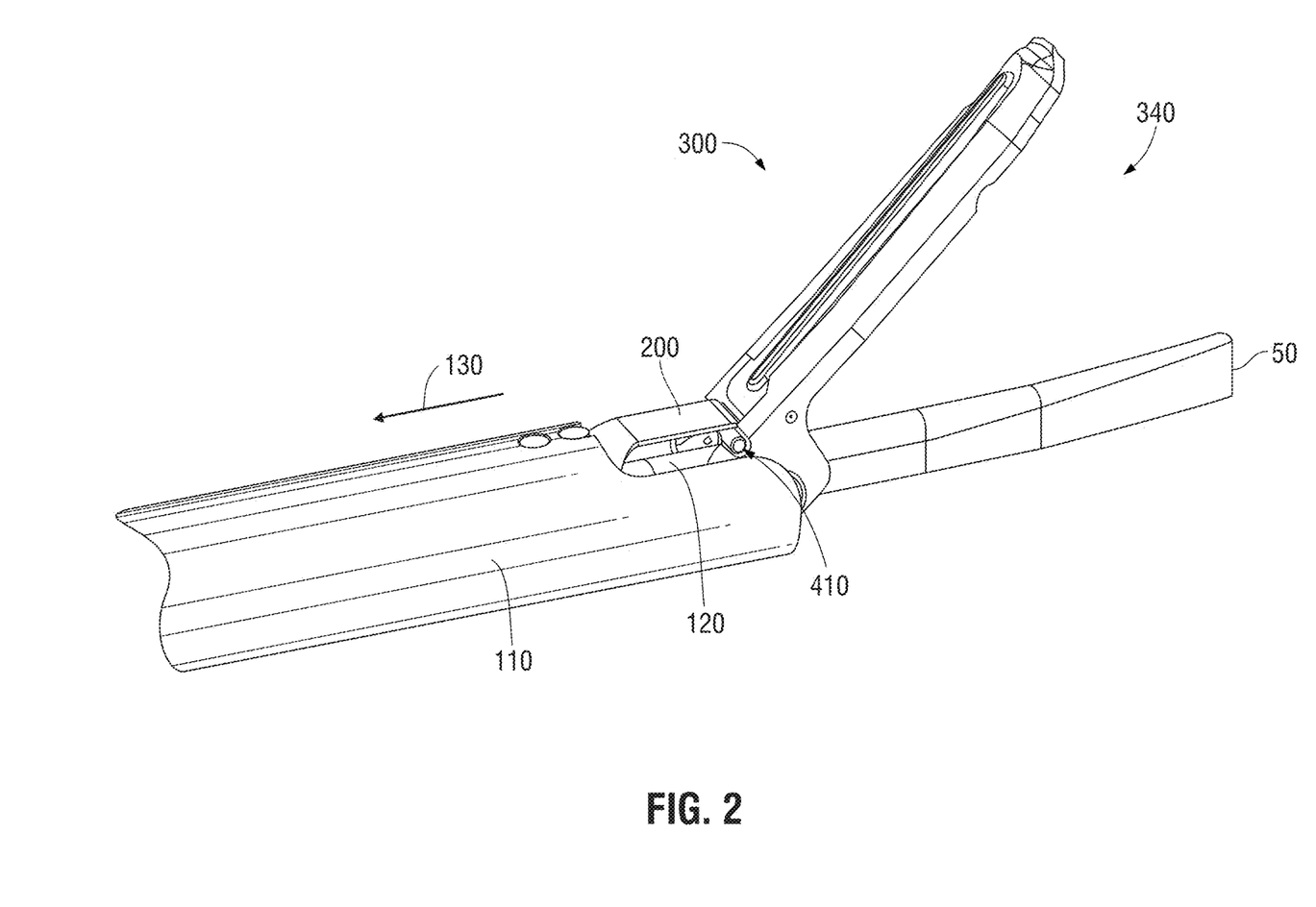
FIG. 2 is an enlarged, perspective view of a distal end portion of the ultrasonic surgical instrument of FIG. 1, wherein the end effector is disposed in the open position.
Figure 3:
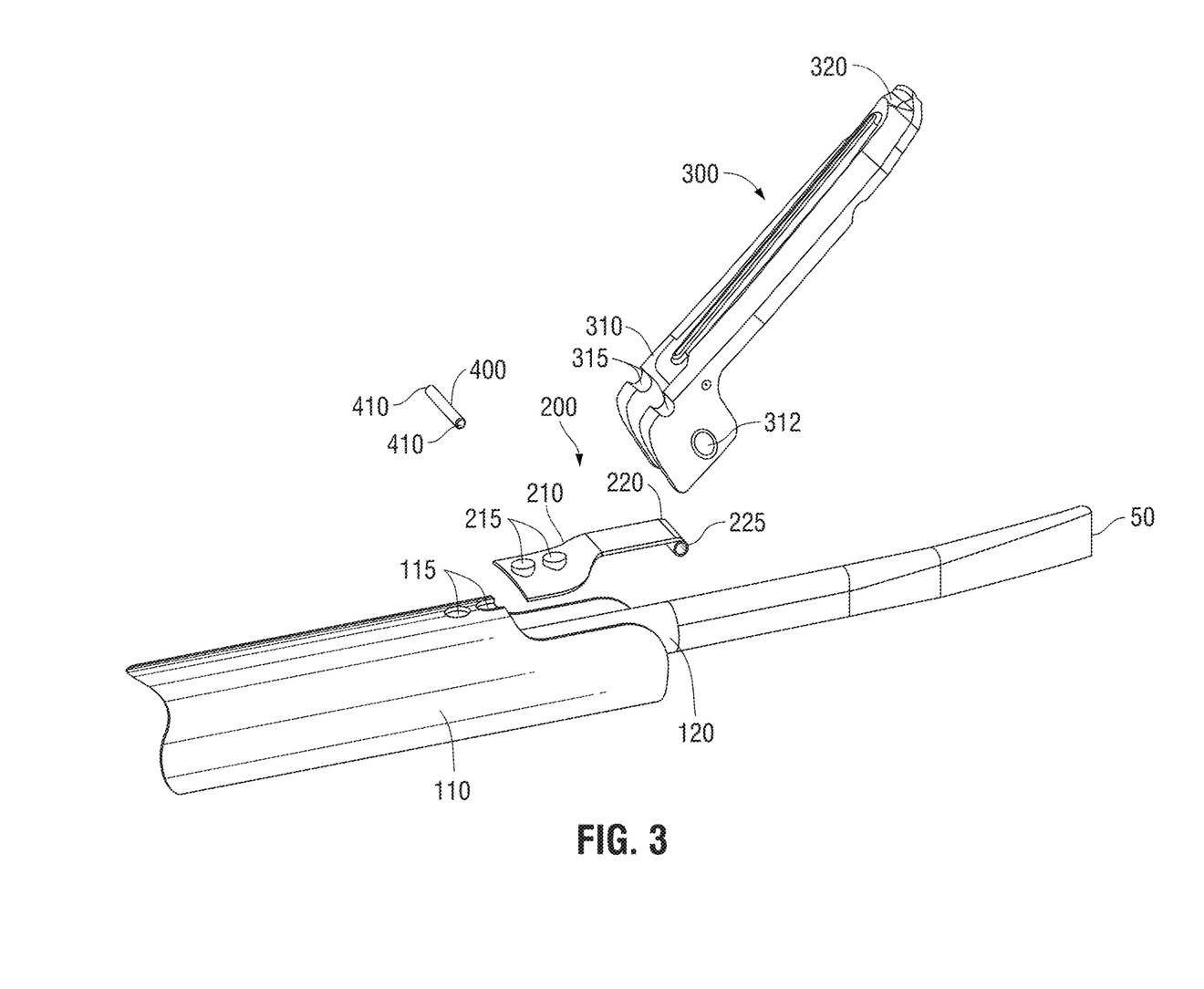
FIG. 3 is an exploded, perspective view of the distal end portion of the ultrasonic surgical instrument of FIG. 1.

Referring to FIGS. 1-3, elongated body portion 100 includes a waveguide 30 which extends from handle assembly 12 to end effector 16. A blade 50 of end effector 16 extends distally from waveguide 30. A proximal end portion of waveguide 30 is configured to engage the ultrasonic transducer of TAG 20 to enable the transmission of ultrasonic energy along waveguide 30 from the ultrasonic transducer of TAG 20 to blade 50. Elongated body portion 100 further includes an inner tube 120 disposed about waveguide 30 and extending between handle assembly 12 and end effector 16. Inner tube 120, more specifically, includes a proximal end portion that extends into handle assembly 12 and a distal end portion including a pair of opposed pivot bosses (not shown) extending outwardly therefrom for pivotable engagement within apertures 312 defined within the spaced-apart proximal flanges of proximal flange portion 310 of jaw member 300 to thereby pivotably mount jaw member 300 at the distal end portion of inner tube 120. As an alternative to pivot bosses disposed on the distal end portion of inner tube 120 and apertures 312 defined within the spaced-apart proximal flanges of proximal flange portion 310 of jaw member 300, the reverse configuration or other suitable pivotable configuration may be provided.

An outer tube 110 is slidably disposed about inner tube 120 such that outer tube 110 moves longitudinally about inner tube 120. Outer tube 110 similarly extends between handle assembly 12 and end effector 16. Outer tube 110, more specifically, includes a proximal end portion that extends into handle assembly 12 and operably couples to clamp trigger 26 by way of a drive assembly (not shown), and a distal end portion that operably couples to proximal flange portion 310 of jaw member 300 via jaw drive arm 200, as detailed below. As a result of this configuration, clamp trigger 26 may be manipulated between an unactuated position and an actuated position to translate outer tube 110 between an advanced position and a retracted position, thereby pivoting jaw member 300 between an open position (FIGS. 1 and 2), wherein jaw member 300 is spaced-apart from blade 50, and a closed position (FIG. 4), wherein jaw member 300 is approximated relative to blade 50. Alternatively, the arrangement of inner and outer tubes 120, 110 may be reversed.

Jaw member 300 includes a proximal flange portion 310 defining a pair of spaced-apart proximal flanges, and a distal body portion 320. The proximal flanges of proximal flange portion 310, as noted above, each defines an aperture 312 therethrough. Each proximal flange of proximal flange portion 310 also defines a groove 315 on an upper surface thereof. Grooves 315 are transversely aligned with one another relative to a longitudinal axis of outer tube 110 and made define semi-circular or other suitable cross-sectional configurations. Distal body portion 310 of jaw member 300 includes a structural support retaining a jaw liner thereon that is configured to oppose blade 50 and clamp tissue therebetween in the closed position of jaw member 300.

Rotation wheel 22 is operably coupled to waveguide 30, inner tube 120, and outer tube 110 such that rotation of rotation wheel 22 relative to handle assembly 12 similarly rotates waveguide 30, inner tube 120, and outer tube 110 relative to handle assembly 12, thereby also rotating blade 50 and jaw member 300 relative to handle assembly 12 in a similar manner. Activation button 24 is configured to selectively activate battery assembly 18 and TAG 20 to produce ultrasonic energy that is transmitted along waveguide 30 to blade 50 of end effector 16.

Figure 4:
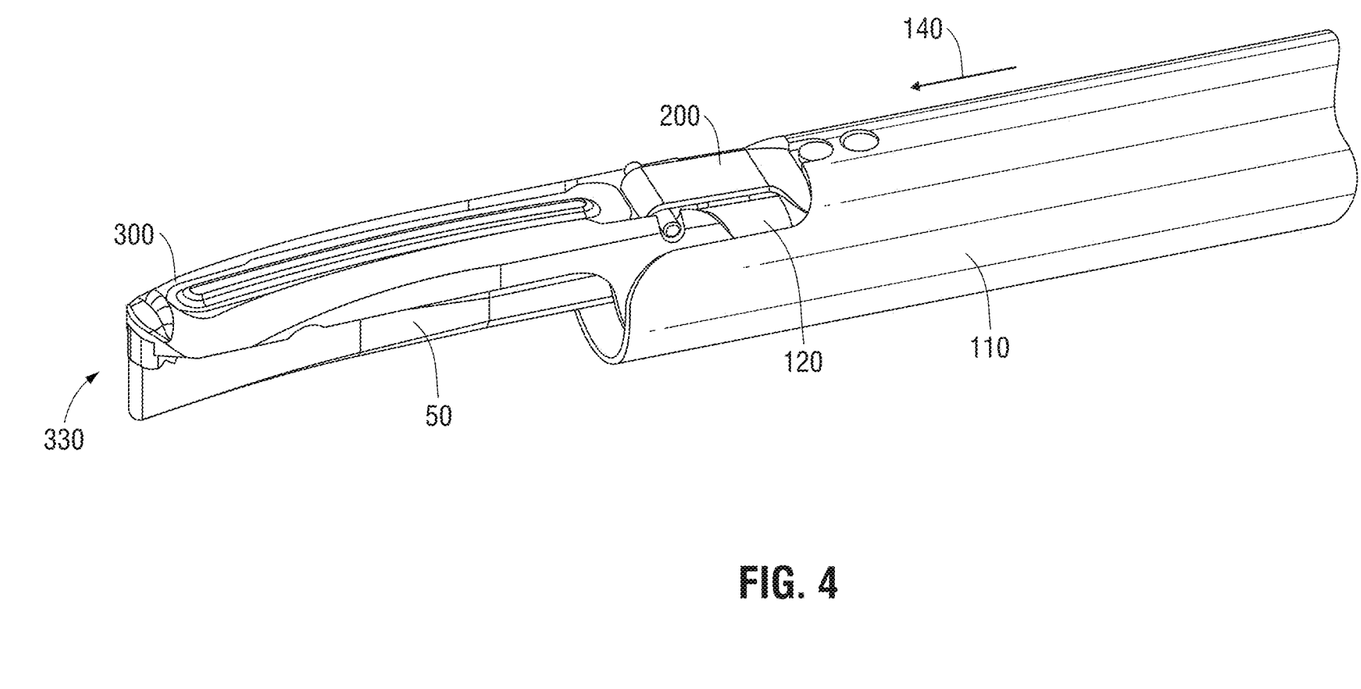
FIG. 4 is an enlarged, perspective view of a distal end portion of the ultrasonic surgical instrument of FIG. 1, wherein the end effector is disposed in the closed position.

Referring to FIGS. 2-4, jaw drive arm 200 operably couples the distal end portion of outer tube 110 with proximal flange portion 310 of jaw member 300. In embodiments, jaw drive arm 200 includes a first end portion 210 fixedly engaged to the outer tube 110 and a second end portion 220 pivotably coupled to the jaw member 300. The jaw drive arm 200 is configured to move longitudinally in tandem, at least initially, with the outer tube 110 such that when the outer tube 110 slides proximally in a first direction 130 (See FIG. 2) about inner tube 120, the jaw drive arm 200 pulls the jaw member 300 to pivot away from the blade 50 toward the open position 340 (FIG. 2). Conversely, when the outer tube 110 slides distally in a second direction 140 (See FIG. 4) the jaw drive arm 200 pushes the jaw member 300 to pivot towards the blade 50 toward the closed position 330 (FIG. 4).

With particular reference to FIG. 3, the first end portion 210 of jaw drive arm 200 includes at least one protruding element 215 disposed on the upper surface thereof and extending upwardly therefrom. In embodiments, a plurality of protruding elements 315 is provided. Correspondingly, at least one fastening aperture 115 is defined through the outer tube 110 and configured to receive the at least one protruding element 215. This configuration allows the jaw drive arm 200 to be removably engaged to the outer tube 110 when the at least one protruding element 215 is inserted into the at least one fastening aperture 115. In some embodiments the at least one fastening aperture 115 and the at least one protruding element 215 are welded together, such that the jaw drive arm 200 is permanently engaged to the outer tube 110. Other suitable engagement configurations, removable or permanent, may also be provided. In embodiments, the jaw drive arm 200 is formed as a single, monolithic piece, e.g., via molding. The jaw drive arm 200 may be formed from a plastic or other suitable material.

In order to couple the jaw member 300 to the jaw drive arm 200, a pivot pin 400 is inserted through a pivot lumen 225 defined at the second end portion 220 of the jaw drive arm 200. The pivot pin 400 defines a length greater than a length of the pivot lumen 225. As a result of this configuration, when the pivot pin 400 is fully inserted into the pivot lumen 225, the opposing ends 410 of the pivot pin 400 protrude from both sides of the pivot lumen 225. The protruding opposed ends 410 of the pivot pin 400 are configured to rest within the grooves 315 defined within the proximal flanges of the flange portion 310 of jaw member 300. Once positioned in this manner, the ends 410 of the pivot pin 400 are welded or otherwise secured within grooves 315 to fix pivot pin 400 relative to jaw member 300 and retain pivot pin 400 in position within pivot lumen 225 while permitting free rotation of pivot pin 400 within pivot lumen 225 and relative to the jaw drive arm 200.

In this configuration, the spacing between the proximal flanges of the proximal flange portion 310 may be greater than the length of the second end portion 220 of the jaw drive arm 200 (which defines the pivot lumen 225), and less than the length of the pivot pin 400.

Accordingly, when the jaw drive arm 200 is translated relative to the jaw member 300, e.g., in response to translation of outer tube 110 about inner tube 120, the pivot pin 400 rotates within the pivot lumen 225 and urges the jaw member 300 to pivot relative to blade 250, e.g., towards the open position 340 when jaw drive arm is pulled proximally in the first direction 130 and towards the closed position 330 when jaw drive arm 200 is pushed distally in the second direction 140.

Figure 5A:
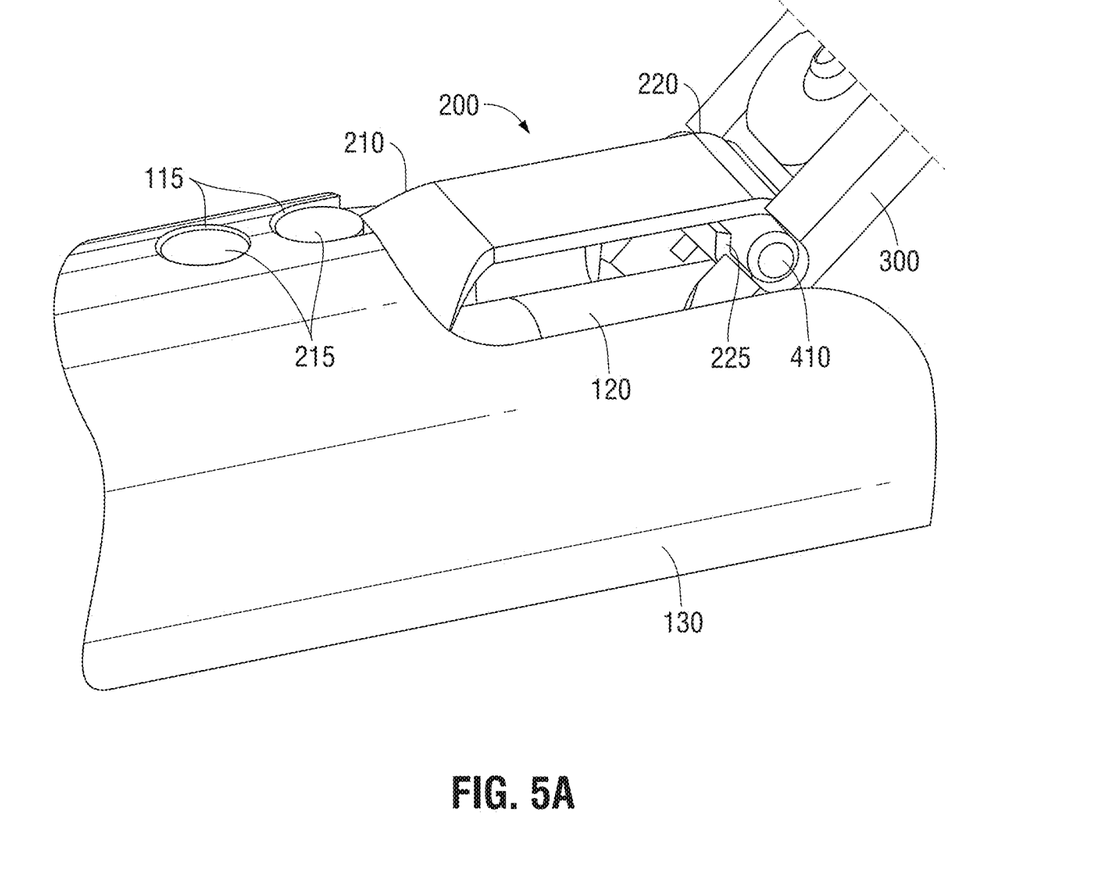
FIG. 5A is a further enlarged, perspective view of a portion of the distal end portion of the ultrasonic surgical instrument of FIG. 1, wherein the end effector is disposed in the open position.
Figure 5B:
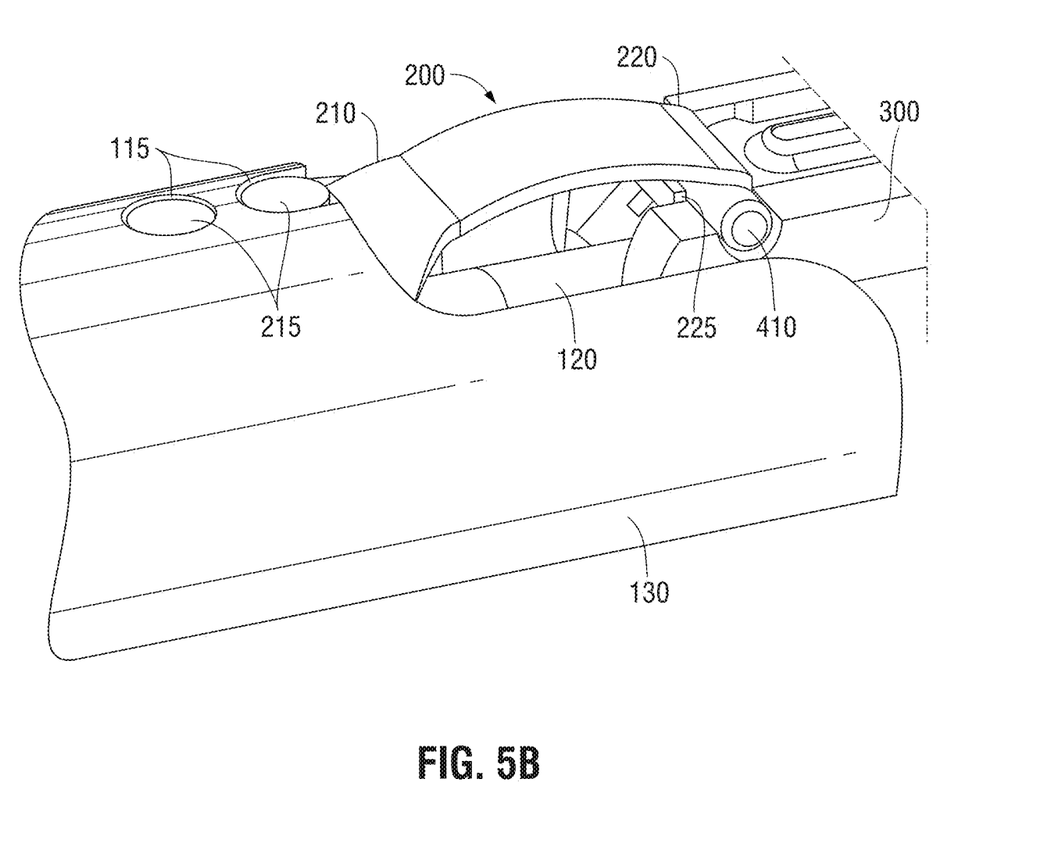
FIG. 5B is a further enlarged, perspective view of a portion of the distal end portion of the ultrasonic surgical instrument of FIG. 1, wherein a pushing force of the outer tube is greater than a threshold force of the drive arm.

FIGS. 5A & 5B, provide close up views of the jaw drive arm 200 in use. In embodiments, the jaw drive arm 200 includes a semi-rigid material configured to flex when compressed beyond a predefined threshold force. The combination of flexible material and geometric design can allow the drive arm 200 to offload excess force exerted by the outer tube 110, thereby inhibiting the excess force from being transmitted to the jaw member 300. In particular, when the force exerted by the outer tube 110 is greater than the predefined threshold force, the jaw drive arm 200 will arch or flex as shown in FIG. 5B (or in any other suitable configuration) to absorb the excess force such that the clamping force being applied by jaw member 300 to tissue clamped between the blade 50 and the jaw member 300 is limited.

To achieve a desired limiting effect on the clamping force, in some embodiments, the jaw drive arm 200 may increase in thickness in a proximal to distal direction from the first end portion 210 until reaching the same height as the outer tube 110 before extending distally toward the second end portion 220 at uniform thickness. Additionally or alternatively, the first end portion 210 of the jaw drive arm 200 can be made wider than the second end portion 220 of the jaw drive arm 200 such that the jaw drive arm 200 tapers inward from the first end portion 210 until reaching the width of the second end portion 220 of the jaw drive arm 200 before extending distally toward the second end portion 220 at uniform width.

While several embodiments of the disclosure have been described above and illustrated in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
    a jaw member;
    a blade;
    an inner tube pivotably supporting the jaw member;
    an outer tube configured to move longitudinally about the inner tube;
    a jaw drive arm having a first end portion engaged with the outer tube and a second end portion defining a pivot lumen; and
    a pivot pin rotatably disposed within the pivot lumen and including ends extending outwardly from each end of the pivot lumen, wherein the ends of the pivot pin are engaged with the jaw member such that longitudinal translation of the outer tube about the inner tube in a first direction pulls the jaw drive arm and the pivot pin to thereby pivot the jaw member away from the blade and such that longitudinal translation of the outer tube about the inner tube in a second direction pushes the jaw drive arm and the pivot pin to thereby pivot the jaw member towards the blade.

2. The surgical instrument according to claim 1, wherein the jaw drive arm comprises a semi-rigid material configured to flex when compressed beyond a predefined threshold force.

3. The surgical instrument according to claim 2, wherein the flexing of the drive arm is configured to offload a pushing force exerted by the outer tube on the jaw member when the pushing force of the outer tube is greater than the predefined threshold force of the drive arm.

4. The surgical instrument according to claim 1, wherein at least one protruding element is disposed on the first end portion of the drive arm and configured to be inserted into at least one fastening aperture defined within the outer tube.

5. The surgical instrument according to claim 4, wherein the at least one fastening aperture is configured to releasably receive the at least one protruding element such that the jaw drive arm is removably engaged to the outer tube.

6. The surgical instrument according to claim 4, wherein the at least one protruding element is welded within the at least one fastening aperture such that the drive arm is permanently engaged to the outer tube.

7. The surgical instrument according to claim 1, wherein the jaw member comprises a proximal flange portion and a distal body portion extending distally from the proximal flange portion, the proximal flange portion defining a pair of spaced-apart flanges.

8. The surgical instrument according to claim 7, wherein each of the pair of spaced-apart flanges defines a groove configured to receive one of the ends of the pivot pin.

9. The surgical instrument according to claim 8, wherein the ends of the pivot pin are welded into the grooves such that the pivot pin is permanently affixed to the proximal flange portion of the jaw member.

10. The surgical instrument according to claim 7, wherein the pivot pin is freely rotatable within the pivot lumen of the jaw drive arm.

11. The surgical instrument according to claim 7, wherein a spacing between the pair of spaced-apart flanges is greater than a width of the second end portion of the drive arm, and less than a length of the pivot pin.

12. The surgical instrument according to claim 1, wherein the drive arm tapers in thickness along at least a portion of a length thereof from the first end portion toward the second end portion.

13. The surgical instrument according to claim 1, wherein the first end portion of the drive arm is wider than the second end portion of the drive arm.

14. The surgical instrument according to claim 13, wherein the drive arm tapers inward along at least a portion of the length thereof from the first end portion towards the second end portion.

* * * * *